United States Patent

Diehr et al.

[11] Patent Number: 4,647,665
[45] Date of Patent: Mar. 3, 1987

[54] PREPARATION OF SULPHONYLISO(THIO)UREAS AND SULPHONYLISOUREAS

[75] Inventors: Hans-Joachim Diehr; Christa Fest, both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld, all of Fed. Rep. of Germany

[73] Assignee: Bayer Aktiengesellschaft, Leverkusen, Fed. Rep. of Germany

[21] Appl. No.: 769,189

[22] Filed: Aug. 23, 1985

[30] Foreign Application Priority Data

Aug. 30, 1984 [DE] Fed. Rep. of Germany ....... 3431923

[51] Int. Cl.$^4$ .................. C07D 253/00; C07D 251/00; C07D 211/72; C07D 333/32
[52] U.S. Cl. .................................... 544/182; 546/294; 546/155; 546/157; 546/153; 546/163; 546/261; 549/65; 549/479; 548/546; 544/194; 544/332; 544/331; 558/4; 558/8; 558/5
[58] Field of Search .......................... 260/453.4, 453.9; 546/294, 155, 157, 153, 163, 261; 549/65, 479; 548/546; 544/194, 182, 332, 331; 558/4, 8, 5

[56] References Cited

U.S. PATENT DOCUMENTS 4,084,001 4/1978 Durant et al. .................... 260/453.4

FOREIGN PATENT DOCUMENTS 0024215 2/1981 European Pat. Off. ............... 558/4
0117014 8/1984 European Pat. Off. ............... 558/4

Primary Examiner—Henry R. Jiles
Assistant Examiner—Robert C. Whittenbaugh
Attorney, Agent, or Firm—Sprung, Horn, Kramer & Woods

[57] ABSTRACT

A process for the preparation of a sulphonyliso(thio)urea of the formula

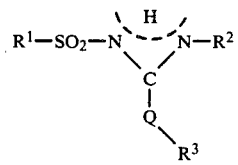

in which
$R^1$ represents an optionally substituted radical from the group consisting of alkyl, aralkyl, aryl and heteroaryl,
$R^2$ represents an optionally substituted and/or optionally fused, six-membered aromatic heterocycle containing at least one nitrogen atom,
$R^3$ represents an optionally substituted radical from the group consisting of alkyl, alkenyl, alkynyl, cycloalkyl, cycloalkyl-alkyl and aralkyl, and
Q represents oxygen or sulphur, comprising reacting a sulphonylguanidine of the formula

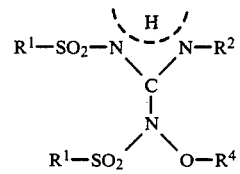

in which
$R^4$ represents an optionally substituted hydrocarbon radical,
with a compound of the formula

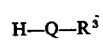

at a temperature between 0° C. and 150° C. The products are known herbicides.

4 Claims, No Drawings

PREPARATION OF SULPHONYLISO(THIO)UREAS AND SULPHONYLISOUREAS

The invention relates to a new process for the preparation of sulphonyliso(thio)ureas.

It is known that certain sulphonylisoureas, for example N'-(4-methoxy-6-methyl-s-triazin-2-yl)-N''-(2-chlorobenzenesulphonyl)-O-methylisourea, are obtained by reacting corresponding sulphonylureas, for example N'-(4-methoxy-6-methyl-s-triazin-2-yl)-N''-(2-chlorobenzenesulphonyl)urea, with triphenylphosphine and carbon tetrachloride and then - without intermediate isolation of the N-sulphonyliminocarbamic acid chlorides formed in this step - with alcohols, for example methanol, or alcoholates, for example sodium methanolate (cf. European Offenlegungsschrift No. 24,215). However, the sulphonylisoureas obtained by this method are very impure and require purification, for example by column chromatography.

It is also known that certain sulphonylisothioureas, for example N'-(4-methoxy-6-methyl-s-triazin-2-yl)-N''-(2,5-dimethoxybenzenesulphonyl)-S-methylisothiourea, are obtained by reacting N-sulphonyliminodithiocarbonic acid esters, for example N-(2,5-dimethoxybenzenesulphonyl)-S',S''-dimethyldithiocarbonic acid esters, with amino compounds, for example 2-amino-4-methoxy-6-methyl-s-triazine, in the presence of bases, for example sodium hydride (cf. European Offenlegungsschrift 5,986). Here again, the sulphonylisothioureas obtained are very impure and purification entails relatively large losses of yield.

A new process has now been found for the preparation of sulphonyliso(thio)ureas of the general formula (I)

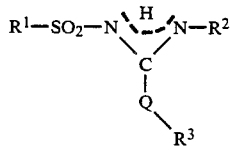

in which $R^1$ represents an optionally substituted radical from the group consisting of alkyl, aralkyl, aryl and heteroaryl, $R^2$ represents an optionally substituted and/or optionally fused six-membered aromatic heterocycle containing at least one nitrogen atom, $R^3$ represents an optionally substituted radical from the group consisting of alkyl, alkenyl, alkynyl, cycloalkyl, cycloalkyl-alkyl and aralkyl, and Q represents oxygen or sulphur, which is characterized in that sulphonylguanidines of the formula (II)

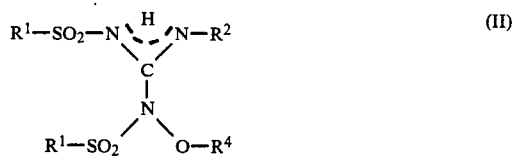

in which $R^1$ and $R^2$ have the meanings given above and $R^4$ represents an optionally substituted hydrocarbon radical, are reacted with compounds of the formula (III)

in which

Q and $R^3$ have the meanings given above, if appropriate in the presence of catalysts and if appropriate in the presence of diluents, at temperatures of between 0° C. and 150° C. It is to be regarded as surprising that the sulphonyliso(thio)ureas of the formula (I) can be prepared by the process according to the invention through selective scission of sulphonylguanidines of the formula (II), because other scission reactions, for example due to attack on the sulphonyl groups, were to be expected in addition to this novel reaction.

If the starting materials used are, for example, N'-(4,6-dimethylpyrimidin-2-yl)-N''-methoxy-N''',N'''-bis(2-methoxycarbonylbenzenesulphonyl)guanidine and ethanethiol, the course of the reaction in the process according to the invention can be outlined by the following equation:

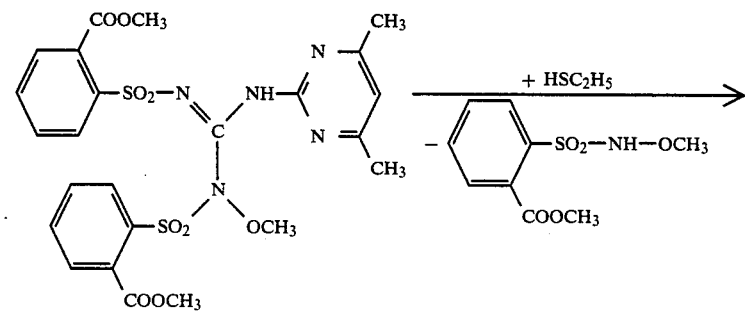

-continued

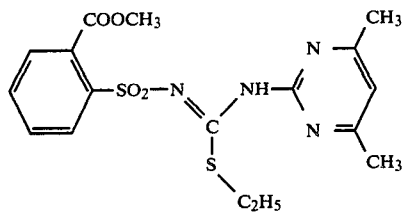

The sulphonylguanidines to be used as starting materials are generally defined by the formula (II).

In the formula (II), $R^1$ preferably represents the radical

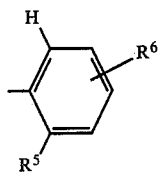

in which $R^5$ and $R^6$ are identical or different and represent hydrogen, halogen [such as, in particular, fluorine, chlorine and/or bromine], cyano, nitro, $C_1$–$C_6$-alkyl [which is optionally substituted by fluorine, chlorine, bromine, cyano, carboxy, $C_1$–$C_4$-alkoxycarbonyl, $C_1$–$C_4$-alkylaminocarbonyl, di($C_4$–$C_4$-alkyl)aminocarbonyl, hydroxy, $C_1$–$C_4$alkoxy, formyloxy, $C_1$–$C_4$-alkylcarbonyloxy, $C_1$–$C_4$-alkoxycarbonyloxy, $C_1$–$C_4$-alkylaminocarbonyloxy, $C_1$–$C_4$-alkylthio, $C_1$–$C_4$-alkylsulphinyl, $C_1$–$C_4$-alkylsulphonyl, di($C_1$–$C_4$-alkyl)aminosulphonyl, $C_3$–$C_6$-cycloalkyl or phenyl], $C_2$–$C_6$-alkenyl [which is optionally substituted by fluorine, chlorine, bromine, cyano, $C_1$–$C_4$-alkoxycarbonyl, carboxy or phenyl], $C_1$–$C_4$-alkoxy [which is optionally substituted by fluorine, chlorine, bromine, cyano, carboxy, $C_1$–$C_4$-alkoxycarbonyl, $C_1$–$C_4$-alkylthio, $C_1$–$C_4$-alkylsulphinyl or $C_1$–$C_4$-alkylsulphonyl], $C_3$–$C_6$-alkenoxy [which is optionally $substituted by fluorine, chlorine, bromine, cyano or $C_1$–$C_4$-alkoxycarbonyl], $C_3$–$C_6$-alkynoxy or the radical $—S(O)_p—R^7$, in which p represents the number zero, 1 or 2 and $R^7$ represents $C_1$–$C_4$-alkyl [which is optionally substituted by fluorine, chlorine, bromine, cyano or $C_1$–$C_4$-alkoxycarbonyl], $C_3$–$C_6$-alkenyl, $C_3$–$C_6$-alkynyl, $C_1$–$C_4$-alkoxy, $C_1$–$C_4$-alkoxyamino, $C_1$–$C_4$-alkoxy-$C_1$–$C_4$-alkylamino, $C_1$–$C_4$-alkylamino or di($C_1$–$C_4$-alkyl)amino, or $R^5$ and $R^6$ represent phenyl or phenoxy, $C_1$–$C_4$-alkylcarbonylamino, $C_1$–$C_4$-alkoxycarbonylamino, $C_1$–$C_4$-alkylaminocarbonylamino, di($C_1$–$C_4$-alkyl)aminocarbonylamino or the radical $—CO—R^8$, in which $R^8$ represents $C_1$–$C_6$-alkyl, $C_1$–$C_6$-alkoxy, $C_3$–$C_6$-alkenoxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkylamino or di($C_1$–$C_4$-alkyl)amino [which are optionally substituted by fluorine and/or chlorine], or $R^5$ and $R^6$ represent $C_1$–$C_4$-alkylsulphonyl oxy, di($C_1$–$C_4$-alkyl)aminosulphonylamino or the radical $—CH=N—R^9$, in which $R^9$ represents $C_1$–$C_6$-alkyl optionally substituted by fluorine, chlorine, cyano, carboxy, $C_1$–$C_4$-alkoxy, carbonyl, $C_1$–$C_4$-alkylthio, $C_1$–$C_4$-alkylsulphinyl or $C_1$–$C_4$-alkylsulphonyl, benzyl optionally substituted by fluorine or chlorine, $C_3$–$C_6$-alkenyl or $C_3$–$C_6$-alkynyl optionally substituted by fluorine or chlorine, phenyl optionally substituted by fluorine, chlorine, bromine, $C_1$–$C_4$-alkyl, $C_1$–$C_4$-alkoxy, trifluoromethyl, trifluoromethoxy or trifluoromethylthio, $C_1$–$C_6$-alkoxy, $C_3$–$C_6$-alkenoxy, $C_3$–$C_6$-alkynoxy or benzyloxy optionally substituted by fluorine and/or chlorine, amino, $C_1$–$C_4$-alkylamino, di($C_1$–$C_4$-alkyl)amino, phenylamino, $C_1$–$C_4$-alkylcarbonylamino, $C_1$–$C_4$-alkoxycarbonylamino, $C_1$–$C_4$-alkylsulphonylamino or phenylsulphonylamino optionally substituted by fluorine, chlorine, bromine or methyl;

$R^1$ also preferably represents the radical

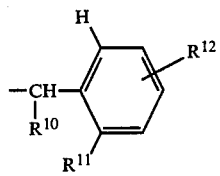

in which $R^{10}$ represents hydrogen or $C_1$–$C_3$-alkyl and $R^{11}$ and $R^{12}$ are identical or different and represent hydrogen, fluorine, chlorine, bromine, nitro, cyano, $C_1$–$C_4$-alkyl [which is optionally substituted by fluorine and/or chlorine], $C_1$–$C_4$-alkoxy [which is optionally substituted by fluorine and/or chlorine], carboxy, $C_1$–$C_4$-alkoxycarbonyl, $C_1$–$C_4$-alkylsulphonyl or di($C_1$–$C_4$-alkyl)aminosulphonyl;

$R^1$ also preferably represents the radical

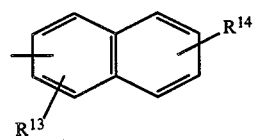

in which $R^{13}$ and $R^{14}$ are identical or different and represent hydrogen, fluorine, chlorine, bromine, nitro, cyano, $C_1$–$C_4$-alkyl [which is optionally substituted by fluorine and/or chlorine] or $C_1$–$C_4$-alkoxy [which is optionally substituted by fluorine and/or chlorine];

$R^1$ also preferably represents the radical

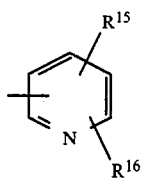

in which
R$^{15}$ and R$^{16}$ are identical or different and represent hydrogen, fluorine, chlorine, bromine, nitro, cyano, C$_1$-C$_4$-alkyl [which is optionally substituted by fluorine and/or chlorine], C$_1$-C$_4$-alkoxy [which is optionally substituted by fluorine and/or chlorine], C$_1$-C$_4$-alkylthio, C$_1$-C$_4$-alkylsulphinyl or C$_1$-C$_4$-alkylsulphonyl [which are optionally substituted by fluorine and/or chlorine], di(C$_1$-C$_4$-alkyl)aminosulphonyl or C$_1$-C$_4$-alkoxycarbonyl;

R$^1$ also preferably represents the radical

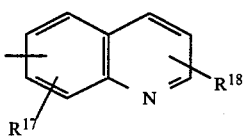

in which
R$^{17}$ and R$^{18}$ are identical or different and represent hydrogen, fluorine, chlorine, bromine, C$_1$-C$_4$-alkyl [which is optionally substituted by fluorine and/or bromine], C$_1$-C$_4$-alkoxy [which is optionally substituted by fluorine and/or chlorine], C$_1$-C$_4$-alkylthio, C$_1$-C$_4$-alkylsulphinyl or C$_1$-C$_4$-alkylsulphonyl [which are optionally substituted by fluorine and/or chlorine] or di(C$_1$-C$_4$-alkyl)aminosulphonyl;

R$^1$ also preferably represents the radical

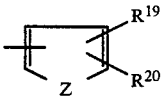

in which
R$^{19}$ and R$^{20}$ are identical or different and represent hydrogen, fluorine, chlorine, bromine, cyano, nitro, C$_1$-C$_4$-alkyl [which is optionally substituted by fluorine and/or chlorine], C$_1$-C$_4$-alkoxy [which is optionally substituted by fluorine and/or chlorine], C$_1$-C$_4$-alkylthio, C$_1$-C$_4$-alkylsulphinyl or C$_1$-C$_4$-alkylsulphonyl [which is optionally substituted by fluorine and/or chlorine], di(C$_1$-C$_4$-alkyl)aminosulphonyl or C$_1$-C$_4$-alkoxycarbonyl, and Z represents oxygen, sulphur or the group N-Z$^1$,
in which
Z$^1$ represents hydrogen, C$_1$-C$_4$-alkyl [which is optionally substituted by fluorine, chlorine, bromine or cyano], C$_3$-C$_6$-cycloalkyl, benzyl, phenyl [which is optionally substituted by fluorine, chlorine, bromine or nitro], C$_1$-C$_4$-alkylcarbonyl, C$_1$-C$_4$-alkoxycarbonyl or di(C$_1$-C$_4$-alkyl)aminocarbonyl;

R$^2$ preferably represents the radical

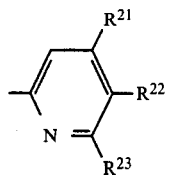

in which
R$^{21}$ and R$^{23}$ are identical or different and represent hydrogen, fluorine, chlorine, bromine, C$_1$-C$_4$-alkyl [which is optionally substituted by fluorine and/or chlorine]or C$_1$-C$_4$-alkoxy [which is optionally substituted by fluorine and/or chlorine], with the proviso that at least one of the radicals R$^{21}$ and R$^{23}$ is other than hydrogen, and
R$^{22}$ represents hydrogen, fluorine, chlorine, bromine, cyano or C$_1$-C$_4$-alkyl [which is optionally substituted by fluorine and/or chlorine];

R$^2$ also preferably represents the radical

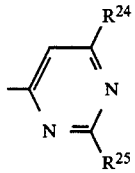

in which
R$^{24}$ and R$^{25}$ are identical or different and represent hydrogen, fluorine, chlorine, bromine, C$_1$-C$_4$-alkyl [which is optionally substituted by fluorine and/or chlorine], C$_1$-C$_4$-alkoxy [which is optionally substituted by fluorine and/or chlorine], C$_1$-C$_4$-alkylamino or di(C$_1$-C$_4$-alkyl)amino, with the proviso that at least one of the radicals R$^{24}$ and R$^{25}$ is other than hydrogen;

R$^2$ also preferably represents the radical

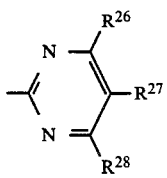

in which
R$^{26}$ represents hydrogen, fluorine, chlorine, bromine, hydroxy, C$_1$-C$_4$-alkyl [which is optionally substituted by fluorine and/or chlorine] or C$_1$-C$_4$-alkoxy [which is optionally substituted by fluorine and/or chlorine], R$^{27}$ represents hydrogen, fluorine, chlorine, bromine, C$_1$-C$_4$-alkyl [which is optionally substituted by fluorine and/or chlorine], cyano, formyl, C$_1$-C$_4$-alkylcarbonyl or C$_1$-C$_4$-alkoxycarbonyl and
R$^{28}$ represents hydrogen, fluorine, chlorine, bromine, hydroxy, C$_1$-C$_4$-alkyl [which is optionally substituted by fluorine and/or chlorine] C$_1$-C$_4$-alkoxy [which is optionally substituted by fluorine and/or chlorine], amino, C$_1$-C$_4$-alkylamino or di(C$_1$-C$_4$-alkyl]amino, or R$^{27}$ and R$^{28}$ together represent C$_3$-C$_4$-alkanediyl;

R$^2$ also preferably represents the radical

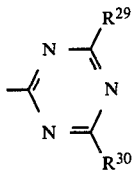

in which
R²⁹ and R³⁰ are identical or different and represent fluorine, chlorine, bromine, hydroxy, C₁–C₄-alkyl [which is optionally substituted by fluorine and/or chlorine], C₃–C₅-cycloalkyl, C₁–C₄-alkoxy [which is optionally substituted by fluorine and/or chlorine], C₁–C₄-alkylthio, C₁–C₄-alkylamino or di(C₁–C₄-alkyl)amino;

R² also preferably represents the radical

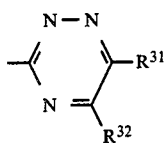

in which
R³¹ and R³² are identical or different and represent hydrogen, methyl or methoxy; and
R⁴ preferably represents C₁–C₄-alkyl or benzyl.

Particular preference is given to starting materials of the formula (II) in which
(A) R¹ represents the radical

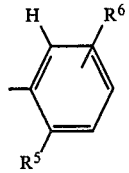

in which
R⁵ represents fluorine, chlorine, bromine, methyl, chloromethyl, trifluoromethyl, methoxy, difluoromethoxy, trifluoromethoxy, methylthio, methylsulphinyl, methylsulphonyl, dimethylaminosulphonyl, phenyl, C₁–C₃-alkoxycarbonyl or C₁–C₃-alkylaminocarbonyl and
R⁶ represents hydrogen;
R² represents the radical

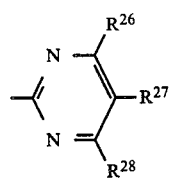

in which
R²⁶ represents hydrogen, methyl, hydroxy, fluorine, chlorine, bromine or methoxy,
R²⁷ represents hydrogen, chlorine, bromine or methyl and
R²⁸ represents C₁–C₃-alkyl, hydroxy, fluorine, chlorine, bromine or C₁–C₃-alkoxy;
and R⁴ represents methyl, or in which (B) R¹ and R⁴ have the meanings given above under (A) and R² represents the radical

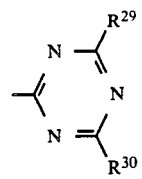

in which
R²⁹ represents fluorine, chlorine, bromine, hydroxy, methyl, cyclopropyl, methoxy, ethoxy, methylthio or ethylthio and
R³⁰ represents fluorine, chlorine, bromine, hydroxy, methyl, cyclopropyl, methoxy, ethoxy, methylamino, ethylamino, dimethylamino or diethylamino.

Examples which may be mentioned of the starting materials of the formula (II) are: N'-(4,6-dimethylpyrimidin-2-yl)-N''-methoxy-N'',N'''-bis(2-chlorobenzenesulphonyl)guanidine, N'-(4,6-dimethylpyrimidin-2-yl)-N''-methoxy-N'',N'''-bis(2-bromobenzenesulphonyl)guanidine, N'-(4,6-dimethylpyrimidin-2-yl)-N''-methoxy-N'',N'''-bis(2fluorobenzenesulphonyl)guanidine, N'-(4,6-dimethylpyrimidin-2-yl)-N''-methoxy-N'',N'''-bis(2-methylbenzenesulphonyl)guanidine, N'-(4,6-dimethylpyrimidin-2-yl)-N''-methoxy-N'',N'''-bis(2-trifluoromethylbenzenesulphonyl)guanidine, N'-(4,6-dimethylpyrimidin-2-yl)-N''-methoxy-N'',N'''-bis(2-methoxybenzenesulphonyl)guanidine, N'-(4,6-dimethylpyrimidin-2-yl)-N''-methoxy-N'',N'''-bis(2-phenylbenzenesulphonyl)guanidine and N'-(4,6-dimethylpyrimidin-2-yl)-N''-methoxy-N'',N'''-bis(2-methoxycarbonylbenzenesulphonyl)guanidine.

The sulphonylguanidines of the formula (II) which are to be used as starting materials are the subject of commonly assigned application Ser. No. 578,345, filed Feb. 9, 1984 now pending corresponding to German Offenlegungsschrift No. 3,334,455 (Le A 22 435) of the art.

The compounds of the formula (II) are obtained by reacting guanidine derivatives of the formula (IV)

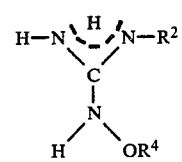  (IV)

in which
R² and R⁴ have the meanings given above, with sulphonyl chlorides of the formula (V)

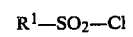

R¹—SO₂—Cl  (V)

in which
R¹ has the meaning given above, in the presence of acid acceptors, for example pyridine or diazabicyclooctane (DABCO), and if appropriate in the presence of diluents, for example methylene chloride or chloroform, at temperatures of between −20° C. and +50° C., preferably at 0° to 30° C. The working-up can be carried out in a conventional manner, for example by treatment with water, if appropriate acidification, for example with hydrochloric acid, extraction with a solvent which is practically immiscible with water, for example methylene chloride or chloroform, washing of the organic phase with water, drying, filtration and concentration. The products of the formula (II) remaining in the residue can generally be crystallized with organic solvents and, if appropriate, purified by recrystallization.

The guanidine derivatives of the formula (IV) required as intermediates are also the subject of the above-identified application Ser. No. 578,345 (German Offenlegungsschrift No. 3,334,455).

These guanidine derivatives are obtained by reacting cyanamino compounds of the formula (VI)

NC—NH—R²      (VI)

in which

R² has the meaning given above, with hydroxylamine derivatives of the formula (VII)

H₂N—OR⁴      (VII)

in which

R⁴ has the meaning given above, or their hydrochlorides, if appropriate in the presence of diluents, for example ethanol or butanol, at temperatures of between 20° C. and 150° C., preferably of between 50° C. and 120° C., and then, if appropriate, treating the reaction product with acid acceptors, for example (aqueous) ammonia, sodium hydroxide or potassium carbonate. The guanidine derivatives (IV) are generally obtained in the form of crystals by this method.

Some of the cyanamino compounds of the formula (VI) are known (cf. J. Chem. Soc. 1953, 1725-1730). These compounds are essentially obtained by the following two synthetic routes:

(1) in general by reacting alkali metal or alkaline earth metal salts of cyanamide—for example sodium cyanamide or calcium cyanamide—with halogen compounds of the formula (VIII)

Hal¹—R²      (VIII)

in which

R² has the meaning given above and

Hal¹ represents fluorine, chlorine, bromine or iodine, in particular chlorine, if appropriate in the presence of inert diluents, for example acetone, acetonitrile or dimethylformamide, at temperatures of between 0° C. and 150° C., preferably of between 10° C. and 100° C.; after the volatile component has been distilled off and the residue dissolved in water, the cyanamino compounds of the formula (VI) can be precipitated by acidification, for example with hydrochloric acid, and isolated by suction filtration; or (2) in the case where R² represents a substituted pyrimidinyl radical, by reacting cyanoguanidine ('dicyandiamide') with β-dicarbonyl compounds, for example acetylacetone (cf. J. Chem. Soc. 1953, 1725-1730), acetoacetic acid ester (cf. J. Pract. Chem. 77 (1908), 542 and J. Chem. Soc. 1948, 586) or malonic acid esters (cf. German Patent Specification No. 158,591). The 2-cyanamino-4-hydroxy-6-methylpyrimidine and 2-cyanamino-4,6-dihydroxypyrimidine obtained from acetoacetic acid esters and malonic acid esters, respectively, can be converted in a known manner to corresponding 2-cyanamino-4-alkoxy-6-methylpyrimidines and 2-cyanamino-4,6-dialkoxypyrimidines, respectively, by reaction with alkylating agents, for example dimethyl or diethyl sulphate, if appropriate in the presence of diluents, for example water, methanol, ethanol, n- and iso-propanol, acetone, dioxane or dimethylformamide, and in the presence of acid-binding agents, for example sodium or potassium hydroxide or sodium or potassium carbonate. To prevent N-alkylation, acylation is carried out, if appropriate, with an acylating agent, for example acetic anhydride or acetyl chloride, and, after alkylation, the product is deacylated again with aqueous acids or bases.

The halogen compounds of the formula (VIII) are known (cf. J. Chem. Soc (C) 1966, 2031; Chem. Pharm. Bull. 11 (1963), 1382-1388; Arch. Pharm. 295 (1962), 649-657).

The hydroxylamine derivatives of the formula (VII) are known or can be prepared by processes known per se (cf. Chem. Pharm. Bull. 15 (1967), 345-349; Bull. Soc. Chim. France 1958, 664; Synthesis 1976, 682).

Some of the sulphonyl chlorides of the formula (V) are known (cf. Chemistry Lett. 1978, 951; European Patent Applications Nos. 23,422, 35,893, 42,731, 44,808, 44,809, 51,466, 64,804 and 70,041; U.S. Pat. Nos. 2,929,820, 4,282,242 and 4,372,778; J. Org. Chem. 33 (1968), 2104). These compounds are essentially obtained by the following two synthetic routes:

(1) by reacting the corresponding sulphonic acids R¹SO₃H or their alkali metal or alkaline earth metal salts with halogenating agents, for example phosphorus(V) chloride (phosphorus pentachloride), phosphoryl chloride (phosphorus oxychloride), thionyl chloride, phosgene or benzotrichloride, if appropriate in the presence of catalysts, for example pyridine or dimethylformamide, and if appropriate using inert diluents, for example methylene chloride, chloroform, acetonitrile, chlorobenzene and/or sulpholane, at temperatures of between −20° C. and +150° C., preferably of between 0° C. and +100° C.; after dilution with water, the sulphonyl chlorides—provided they are obtained in the form of crystals—can be isolated by suction filtration or purified by extraction with a waterimmiscible solvent, for example methylene chloride, diethyl ether or hexane, washing and drying of the extracts, concentration and recrystallization or distillation; or alternatively (2) in a manner known per se (cf. J. Org. Chem. 25 (1960), 1824; German Offenlegungsschrift No. 2,308,262 and European Patent Application No. 59,241) by reacting corresponding amino compounds R¹-NH₂ with sodium nitrite and hydrochloric acid, if appropriate in the presence of acetic acid, at temperatures of between −10° C. and +20° C., preferably of between −5° C. and then reacting the product (in situ) with sulphur dioxide or a salt of sulphurous acid, for example sodium sulphite or sodium bisulphite, in the presence of a copper compound as a catalyst, for example copper chloride or copper sulphate, at temperatures of between 0° C. and 80° C., preferably of between 10° C. and 60° C.

Working-up can be carried out in a conventional manner: on dilution with water, the sulphonyl chlorides are generally obtained in the form of crystals and can be isolated by suction filtration. However, they can also be extracted from the aqueous dispersion with a solvent which is practically immiscible with water, for example methylene chloride or diethyl ether, dried and purified by vacuum distillation.

The other compounds to be used as starting materials in the process according to the invention are generally defined by the formula (III).

In the formula (III),

Q preferably represents oxygen or sulphur and
$R^3$ preferably represents $C_1$-$C_{12}$-alkyl [which is optionally substituted by fluorine, chlorine, bromine, cyano, nitro, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkylcarbonyl, $C_1$-$C_4$-alkoxycarbonyl, $C_1$-$C_4$-alkylaminocarbonyl or di($C_1$-$C_4$-alkyl)aminocarbonyl], $C_3$-$C_6$-alkenyl, $C_3$-$C_6$-alkynyl, $C_3$-$C_6$-cycloalkyl, $C_3$-$C_6$-cycloalkyl-$C_1$-$C_2$-alkyl or phenyl-$C_1$-$C_2$-alkyl [which is optionally substituted by fluorine, chlorine, nitro, cyano, $C_1$-$C_4$-alkyl, $C_1$-$C_4$-alkoxy or $C_1$-$C_4$-alkoxycarbonyl].

Particularly preferred starting materials of the formula (III) are those in which (A) Q represents oxygen and $R^3$ represents $C_1$-$C_6$-alkyl [which is optionally substituted by fluorine, chlorine, cyano, $C_1$-$C_2$-alkoxy or $C_1$-$C_2$-alkoxycarbonyl], $C_3$-$C_4$-alkenyl, $C_3$-$C_4$-alkynyl or benzyl [which is optionally substituted by fluorine, chlorine, nitro, cyano, methyl, methoxy or $C_1$-$C_2$-alkoxycarbonyl], or (B) Q represents sulphur and $R^3$ has the meaning given under (A).

Examples which may be mentioned of the starting materials of the formula (III) are: methanol, ethanol, propanol, isopropanol, butanol, isobutanol, sec.-butanol, pentanol, isopentanol, sec.-pentanol, hexanol, 2-fluoroethanol, 2,2,2-trifluoroethanol, 2-chloroethanol, 3-chloropropanol, 2-cyanoethanol, 2-methoxyethanol, 2-ethoxyethanol, methyl hydroxyacetate, ethyl hydroxyacetate, ethyl lactate, ethyl lactate, allyl alcohol, crotyl alcohol, propargyl alcohol, benzyl alcohol, 4-fluorobenzyl, 4-chlorobenzyl, 4-nitrobenzyl, 4-cyanobenzyl, 4-methylbenzyl, 4-methoxybenzyl, 4-methoxycarbonylbenzyl or 4-ethoxycarbonylbenzyl alcohol, and also methanethiol, methanethiol, propanethiol, 1-methylethanethiol, butanethiol, 2-methylpropanethiol, 1-methylpropanethiol, ethyl mercaptoacetate and benzylmercaptan.

The starting materials of the formula (III) are known.

The process according to the invention is optionally carried out in the presence of diluents. Possible diluents are virtually all inert organic solvents, but preferably aprotic or protic polar solvents. These include chlorinated hydrocarbons, for example methylene chloride, chloroform and chlorobenzene, ketones, for example acetone, methyl ethyl ketone, methyl isopropyl ketone and methyl isobutyl ketone, nitriles, for example acetonitrile and propionitrile, ethers, for example diethyl ether, diisopropyl ether, dimethoxyethane, tetrahydrofuran and dioxane, amides, for example dimethylformamide and dimethylacetamide, and also dimethyl sulphoxide and sulpholane.

If hydroxyl compounds of the formula (III)—Q represents oxygen—are used as starting materials, it is preferred to use an excess thereof and these compounds then serve simultaneously as diluents.

The process according to the invention is optionally carried out in the pre$ence of catalysts. It is preferred to use catalysts when using hydroxyl compounds of the formula (III)—Q represents oxygen.

Suitable catalysts for the process according to the invention are nucleophilic nitrogen compounds having practically no tendency or only a very slight tendency to donate protons. These compounds include trialkylamines, for example trimethylamine, triethylamine, tripropylamine and tributylamine, dialkylaralkylamines, for example N,N-dimethylbenzylamine and N,N-diethylbenzylamine, dialkylarylamines, for example N,N-dimethylaniline and N,N-diethylaniline, and also nitrogen heterocycles, for example pyrazole, 3,5-dimethylpyrazole, imidazole, 1-methylimidazole, 2-methylimidazole, triazole, pyridine, 4-dimethylaminopyridine and diazabicyclooctane (DABCO).

The reaction temperatures in the process according to the invention can be varied within a relatively wide range. In general, the process is carried out at between 0° C. and 150° C., preferably at between 20° C. and 120° C.

The process according to the invention is generally carried out at normal pressure or a very slightly elevated pressure of between 750 and 1000 mm Hg (997–1330 mbar).

To carry out the process according to the invention in general between 1 and 100 mol, preferably between 2 and 50 mol, of the compound of the formula (III) and, if appropriate, between 0.01 and 5 mol, preferably between 0.1 and 3 mol, of a catalyst are used per mol of sulphonylguanidine of the formula (II).

The reaction components are usually brought together at room temperature and the reaction mixture is stirred until the reaction has ended. If the products are then obtained in the form of crystals, they can be isolated by suction filtration. Otherwise, the mixture is concentrated and the residue is crystallized by digestion with a suitable solvent.

The sulphonyliso(thio)ureas of the formula (I) to be prepared by the process according to the invention can be used as herbicides (cf. European Offenlegungsschriften No. 5,986 and 24,215).

PREPARATION EXAMPLES

Example 1

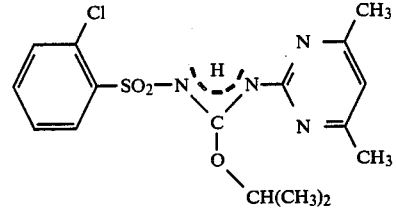

A mixture of 5.5 g (0.01 mol) of N'-(4,6-dimethylpyrimidin-2-yl)-N''-methoxy-N'',N'''-bis(2-chlorobenzenesulphonyl)guanidine, 3,0 g (0.03 mol) of triethylamine and 25 ml of isopropanol is stirred for 5 hours at 50° C. The product obtained in the form of crystals on cooling is isolated by suction filtration.

This gives 3.0 g (78% of theory) of N'-(4,6- dimethylpyrimidin-2-yl)-N''-(2-chlorobenzenesulphonyl)-O-(1-methylethyl)isourea of melting point 145° C.

Example 2

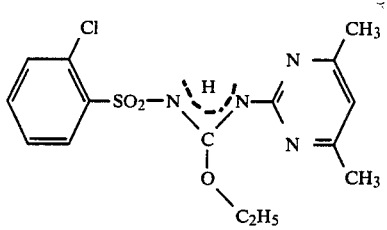

A mixture of 13.8 g (0.025 mol) of N'-(4,6-dimethyl-pyrimidin-2-yl)-N''-methoxy-N'',N'''-bis(2-chlorobenzenesulphonyl)guanidine, 1.8 g (0.0265 mol) of pyrazole and 60 ml of ethanol is boiled under reflux for 5 hours. It is then concentrated and the residue is triturated with methanol. The product thus obtained in the form of crystals is isolated by suction filtration.

This gives 4.0 g (45% of theory) of N'-(4,6-dimethyl-pyrimidin-2-yl)-N''-(2-chlorobenzenesulphonyl)-O-ethylisourea of melting point 126° C.

The compounds of the formula (I) listed in Table 1 below can be prepared analogously:

TABLE 1

$$R^1-SO_2-N\overset{H}{\underset{\underset{O}{\overset{|}{C}}}{\cdots}}N-R^2 \qquad (I)$$
$$\phantom{R^1-SO_2-N}\underset{R^3}{|}$$

| Example No. | $R^1$ | $R^2$ | $R^3$ | Q | Melting point (°C.) |
|---|---|---|---|---|---|
| 3 | 2-Cl-C$_6$H$_4$ | 4,6-dimethylpyrimidin-2-yl | —CH$_3$ | O | 115 |
| 4 | 2-COOCH$_3$-C$_6$H$_4$ | 4,6-dimethylpyrimidin-2-yl | —CH(CH$_3$)$_2$ | O | 83 |
| 5 | 2-COOCH$_3$-C$_6$H$_4$ | 4,6-dimethylpyrimidin-2-yl | —CH$_2$CH$_2$Cl | O | 125 |
| 6 | 2-Cl-C$_6$H$_4$ | 4,6-dimethylpyrimidin-2-yl | —CH$_2$CH$_2$Cl | O | 152 |
| 7 | 2-COOCH$_3$-C$_6$H$_4$ | 4,6-dimethylpyrimidin-2-yl | —CH$_3$ | O | 105 |
| 8 | 2-COOCH$_3$-C$_6$H$_4$ | 4,6-dimethylpyrimidin-2-yl | —CH$_2$CF$_3$ | O | 35 |

TABLE 1-continued $$R^1-SO_2-N\underset{\underset{\underset{R^3}{O}}{C}}{\overset{H}{\diagdown}}N-R^2 \quad (I)$$

| Example No. | R¹ | R² | R³ | Q | Melting point (°C.) |
|---|---|---|---|---|---|
| 9 | 2-Cl-C₆H₄- | 4,6-dimethylpyrimidin-2-yl | —CH₂COOCH₃ | S | 202 |
| 10 | 2-COOCH₃-C₆H₄- | 4,6-dimethylpyrimidin-2-yl | —C₂H₅ | O | (amorphous) |

PREPARATION OF STARTING MATERIALS OF THE FORMULA (II)

Example (II-1)

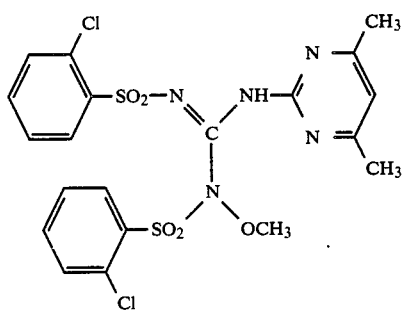

A mixture of 29.4 g (0.15 mol) of N'-(4,6-dimethylpyrimidin-2-yl)-N'''-methoxyguanidine, 63.6 g (0.3 mol) of 2-chlorobenzenesulphonyl chloride and 150 ml of pyridine is stirred for 2 days at 20° C. After the pyridine has been substantially distilled off under a water-jet vacuum, the residue is treated with 200 ml of water and extracted with 200 ml of methylene chloride. The organic phase is separated off, dried and concentrated. The residue is crystallized by digestion with ethanol.

This gives 41.2 g (51% of theory) of N'-(4,6-dimethylpyrimidin-2-yl)-N'''-methoxy-N'',N'''-bis(2-chlorobenzenesulphonyl)guanidine of melting point 164° C. to 166° C.

The compounds of the formula (II) listed in Table 2 below can be prepared analogously:

TABLE 2

$$R^1-SO_2-N\underset{\underset{\underset{O-R^4}{N}}{C}}{\overset{H}{\diagdown}}N-R^2 \quad (II)$$
$$R^1-SO_2$$

| Example No. | R¹ | R² | R⁴ | Melting point (°C.) |
|---|---|---|---|---|
| (II-2) | 2-COOCH₃-C₆H₄- | 4,6-dimethylpyrimidin-2-yl | CH₃ | 165 |
| (II-3) | 2-CH₃-C₆H₄- | 4,6-dimethylpyrimidin-2-yl | CH₃ | 129 |
| (II-4) | 2-phenyl-C₆H₄- | 4,6-dimethylpyrimidin-2-yl | CH₃ | 171 |
| (II-5) | 2-CF₃-C₆H₄- | 4,6-dimethylpyrimidin-2-yl | CH₃ | 121 |

TABLE 2-continued $$R^1-SO_2-N\overset{H}{\underset{\underset{R^1-SO_2}{\overset{|}{C}}}{\cdots}}N-R^2 \qquad (II)$$
$$\phantom{R^1-SO_2-N}O-R^4$$

| Example No. | $R^1$ | $R^2$ | $R^4$ | Melting point (°C.) |
|---|---|---|---|---|
| (II-6) | 2-Br-C$_6$H$_4$ | 4,6-dimethylpyrimidin-2-yl | CH$_3$ | 147 |
| (II-7) | 2-F-C$_6$H$_4$ | 4,6-dimethylpyrimidin-2-yl | CH$_3$ | 166 |
| (II-8) | 2-OCH$_3$-C$_6$H$_4$ | 4,6-dimethylpyrimidin-2-yl | CH$_3$ | 196 |
| (II-9) | 2-OCF$_3$-C$_6$H$_4$ | 4,6-dimethylpyrimidin-2-yl | CH$_3$ | 158 |
| (II-10) | 2-OCHF$_2$-C$_6$H$_4$ | 4,6-dimethylpyrimidin-2-yl | CH$_3$ | 163 |
| (II-11) | 2-SCH$_3$-C$_6$H$_4$ | 4,6-dimethylpyrimidin-2-yl | CH$_3$ | 155 |
| (II-12) | 2-SO$_2$N(CH$_3$)$_2$-C$_6$H$_4$ | 4,6-dimethylpyrimidin-2-yl | CH$_3$ | 138 |
| (II-13) | 2-COOC$_2$H$_5$-C$_6$H$_4$ | 4,6-dimethylpyrimidin-2-yl | CH$_3$ | 106 |
| (II-14) | 2-COOC$_4$H$_9$-n-C$_6$H$_4$ | 4,6-dimethylpyrimidin-2-yl | CH$_3$ | 104 |
| (II-15) | 2-COOC$_3$H$_7$-n-C$_6$H$_4$ | 4,6-dimethylpyrimidin-2-yl | CH$_3$ | 134 |
| (II-16) | 2-SO$_2$CH$_3$-C$_6$H$_4$ | 4,6-dimethylpyrimidin-2-yl | CH$_3$ | — |

PREPARATION OF STARTING MATERIALS OF THE FORMULA (IV)

Example (IV-1)

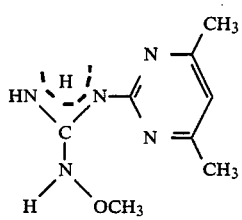

A mixture of 109 g (0.67 mol) of O-methylhydroxylamine hydrochloride, 99 g (0.67 mol) of 2-cyanamino-4,6-dimethylpyrimidine and 600 ml of ethanol is boiled under reflux for 7 hours. The alcohol is then distilled off under a water-jet vacuum, the residue is dissolved in hot water and this solution is added to 100 ml of concentrated aqueous ammonia. The product which crystallizes out is filtered off with suction and recrystallized from ethanol.

This gives 71.8 g (55% of theory) of N'-(4,6-dimethylpyrimidin-2-yl)-N''-methoxyguanidine of melting point 134° C. to 136° C.

PREPARATION OF STARTING MATERIALS OF THE FORMULA (V)

Example (V-1)

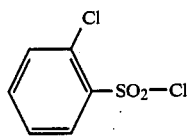

295 ml of phosphoryl chloride ('phosphorus oxychloride') are added dropwise, at 20° C. to 30° C., to a mixture of 172 g (0.8 mol) of sodium 2-chlorobenzenesulphonate, 300 ml of acetonitrile and 300 ml of sulpholane. The reaction mixture is stirred for 4 hours at 70° C. and then cooled to 5° C. and diluted with ice-water. After extraction with petroleum ether, washing of the extraction solution with water, drying, filtration and concentration, the product remaining in the residue is purified by vacuum distillation.

This gives 117 g (70% of theory) of 2-chlorobenzenesulphonyl chloride of boiling point 110° C./1.1 mbar.

Example (V-2)

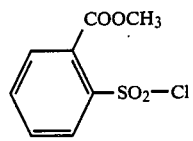

75 g (0.5 mol) of methyl 2-aminobenzoate are dissolved in 176 ml of concentrated hydrochloric acid and 100 ml of acetic acid. A solution of 34.4 g of sodium nitrite in 70 ml of water is added dropwise at 0° C. After stirring for a further 15 minutes, the reaction mixture is slowly added to a saturated solution of sulphur dioxide in 450 ml of acetic acid, cooled to 0° C. After removal of the cooling bath, the mixture is stirred until the evolution of gas has ended, 10 g of copper(II) chloride being introduced in portions during this period. After dilution with ice-water, extraction with methylene chloride, washing of the extraction solution with water, drying, filtration and concentration, the product remaining in the residue is purified by vacuum distillation.

This gives 45 g (38% of theory) of 2-methoxycarbonylbenzenesulphonyl chloride of boiling point 150° C./1.33 mbar.

The compounds of the formula (V) listed in Table 3 below can be prepared analogously:

TABLE 3

$R^1$—$SO_2$—Cl    (V)

| Example No. | $R^1$ | Boiling point/pressure |
|---|---|---|
| (V-2) | OCH$_3$ (ortho-substituted phenyl) | (oil, decomposes on distillation) |
| (V-3) | phenyl (ortho-substituted phenyl) | [melting point: 100° C.] |
| (V-4) | CF$_3$ (ortho-substituted phenyl) | (oil) |
| (V-5) | Br (ortho-substituted phenyl) | 142° C./4 mbar |
| (V-6) | F (ortho-substituted phenyl) | 106° C./4 mbar |
| (V-7) | OCF$_3$ (ortho-substituted phenyl) | [melting point: 32° C.] |
| (V-8) | OCHF$_2$ (ortho-substituted phenyl) | (oil, decomposes on distillation) |
| (V-9) | SO$_2$N(CH$_3$)$_2$ (ortho-substituted phenyl) | [melting point: 103° C.] |
| (V-10) | SCH$_3$ (ortho-substituted phenyl) | (oil, decomposes on distillation) |
| (V-11) | SCH(CH$_3$)$_2$ (ortho-substituted phenyl) | 90° C./1.33 mbar |
| (V-12) | CH$_2$SO$_2$CH$_3$ (ortho-substituted phenyl) | [melting point: 120° C.] |

TABLE 3-continued $$R^1\text{—}SO_2\text{—}Cl \qquad (V)$$

| Example No. | $R^1$ | Boiling point/pressure |
|---|---|---|
| (V-13) | 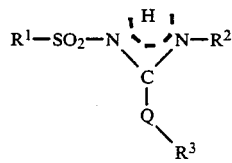 COOC$_2$H$_5$ | 155° C./5.32 mbar |

It will be understood that the specification and examples are illustrative but not limitative of the present invention and that other embodiments within the spirit and scope of the invention will suggest themselves to those skilled in the art.

We claim:

1. A process for the preparation of a sulphonyliso(thio)urea of the formula

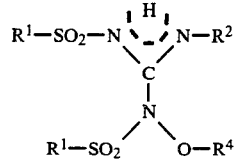

in which
R$^1$ represents an optionally substituted radical from the group consisting of alkyl, aralkyl, aryl and heteroaryl,
R$^2$ represents an optionally substituted and/or optionally fused, six-membered aromatic heterocycle containing at least one nitrogen atom,
R$^3$ represents an optionally substituted radical from the group consisting of alkyl, alkenyl, alkynyl, cycloalkyl, cycloalkyl-alkyl and aralkyl, and
Q represents oxygen or sulphur,
comprising reacting a sulphonylguanidine of the formula $$\begin{array}{c} \text{H} \\ R^1\text{—}SO_2\text{—}N\diagdown\diagup N\text{—}R^2 \\ \diagdown C \diagup \\ | \\ N \\ \diagup \quad \diagdown \\ R^1\text{—}SO_2 \quad O\text{—}R^4 \end{array}$$

in which
R$^4$ represents an optionally substituted hydrocarbon radical,
with a compound of the formula $$H\text{—}Q\text{—}R^3$$

at a temperature between 0° C. and 150° C.

2. A process according to claim 1, wherein the reaction is effected in the presence of a catalyst comprising a nucleophilic nitrogen compound with at most a slight tendency to donate protons.

3. A process according to claim 1, wherein the reaction is effected in the presence of a catalyst selected from the group consisting of a trialkylamine, a dialkylaralkylamine, a dialkylarylamine and a basic nitrogen-containing heterocyclic.

4. A process according to claim 1, wherein the reaction is effected in the presence of a catalyst selected from the group consisting of trimethylamine, triethylamine, tripropylamine, tributylamine, N,N-dimethylbenzylamine, N,N-diethylbenzylamine, N,N-dimethylaniline, N,N-diethylaniline, pyrazole, 3,5-dimethylpyrazole, imidazole, 1-methylimidazole, 2-methylimidazole, triazole, pyridine, 4-dimethylaminopyridine and diazabicyclooctane.

* * * * *